United States Patent [19]

Sugimori et al.

[11] Patent Number: 5,296,360
[45] Date of Patent: Mar. 22, 1994

[54] PROCESS FOR PRODUCING GANGLIOSIDE $G_{M1}$

[75] Inventors: Tsunetake Sugimori, Uji; Yoji Tsukada, Kyoto; Yasuhiro Ohta, Uji, all of Japan

[73] Assignee: Marukin Shoyu Co., Ltd., Japan

[21] Appl. No.: 679,087

[22] PCT Filed: Oct. 30, 1989

[86] PCT No.: PCT/JP89/01118

§ 371 Date: Jun. 28, 1991

§ 102(e) Date: Jun. 28, 1991

[87] PCT Pub. No.: WO91/06663

PCT Pub. Date: May 16, 1991

[51] Int. Cl.$^5$ .............................. C12P 19/04
[52] U.S. Cl. ........................ 435/101; 435/74; 435/84; 536/55; 536/55.3; 424/94.6; 424/94.61
[58] Field of Search ............... 424/94.6, 94.61; 435/84, 101, 74; 536/55, 55.3

[56] References Cited

U.S. PATENT DOCUMENTS 4,071,408 1/1978 Flashner et al. .................. 435/830
5,116,752 5/1992 Sugimori et al. .................. 455/200

OTHER PUBLICATIONS

Genetics, vol. 114, No. 1, (1986), pp. 247-258, published in 1986 and authored by P. B. Samollow et al.
Chemical Abstracts, vol. 103, No. 11, (Sep. 16, 1985) p. 320, Abstract No. 84523d, published in U.S.A. and authored by Saito Megumi et al.
Chemical Abstracts, vol. 63, No. 8 (Oct. 11, 1965), Abstract No. 10399g, published in U.S.A. and authored by Suzuki Kunihiko et al.
Uchida et al; J. Biochem. 86:1573-1585 (1979).
Corfield et al; Perspectives in Inherited Metabolic Diseases 4:3-70 (1981).
Sugano et al; Febs Lett. 89(2):321-325 (1978).
Saito et al; J. Biol. Chem. 254(16):7845-7854 (1979).
Suzuki et al; Biochim. Biophys. Acta 619:632-639 (1980).
Macher et al; J. Biol. Chem. 256(4):1968-1974 (1981).
Sander-Wewer et al; Chemical Abstracts 98:493679q (1983).
Saito et al; Anal. Biochem. 148:54-58 (1985).
Wieraszko et al; Chemical Abstracts 104:204605b (1986); 107:151908f (1987).
Sonnino et al; Chemical Abstracts 108:204912q (1988).

*Primary Examiner*—Johnnie R. Brown
*Assistant Examiner*—Pamela S. Webber
*Attorney, Agent, or Firm*—Larson and Taylor

[57] ABSTRACT

The present invention provides a process for preparing ganglioside $G_{M1}$ characterized in that neuraminidase isozyme S is allowed to act on gangliosides to produce ganglioside $G_{M1}$.

10 Claims, No Drawings

PROCESS FOR PRODUCING GANGLIOSIDE $G_{M1}$

DESCRIPTION

1. Technical Field

This invention relates to a process for producing ganglioside $G_{M1}$.

2. Prior Art

"Ganglioside" is a general name of the group of sialic acid-containing sphingoglycolipids and is known to exist in the brain of higher animals, especially in the nervous system. In the living body, the gangliosides not only take part in nervous function and recognition, differentiation, proliferation, canceration, senescence, etc. of cells, but also, from a cell sociological view point, are responsible for receptor function of cytotoxins such as cholera toxin and botulinum toxin, peptide hormones such as thyroid hormone, interferons and so on. The gangliosides are also supposed to contribute to negative charges on the surface of cells. In fact, it is reported that the gangliosides extracted from bovine brain promote regeneration of damaged peripheral nerve and useful for treatment of alcoholic polyneuritis, diabetic neuropathy, etc (Iyaku to Yakugaku, 13(6), pp 1407-1412 (1985); Practice, 4(4), pp 452-456 (1987); Iyaku Journal, 22(7), pp 55-62 (1986)).

As described above, gangliosides are important substances having various functions in the living body. Therefore, it is desired to establish a process for collecting each of various gangliosides in a pure form. In order to prepare a specific ganglioside, conventionally attempted are methods using various kinds of chromatography. However, since the starting material, i.e., ganglioside components as extracted from bovine brain or the like is a mixture containing various gangliosides each in trace amounts, it is difficult to obtain the desired products even by conducting cumbersome procedures, and any proper purification methods have not been found yet. Further, although an attempt is made to synthesize gangliosides by chemical technique, its process is complicated and side reactions are likely to occur, entailing difficulty in removing by-products.

On the other hand, neuraminidase is an enzyme which has been considered not to act directly on the gangliosides on its own. As a matter of fact, it is only reported that asialoganglioside $G_{A1}$ is formed from ganglioside $G_{M1}$ in the presence of detergents such as cholates (Masaki Saito, Taisha, 16, p 761 (1977)). Moreover, it has been not known at all that any isozyme of the neuraminidase exists.

DISCLOSURE OF THE INVENTION

An object of the present invention is to provide a process for collecting a specific ganglioside, i.e., ganglioside $G_{M1}$ from gangliosides.

Another object of the present invention is to provide a process for producing ganglioside $G_{M1}$ in high purity and in good yield.

Namely, the present invention provides a process for producing ganglioside $G_{M1}$ characterized in that neuraminidase isozyme S is allowed to act on gangliosides to obtain ganglioside $G_{M1}$.

The present inventors have conducted intensive research and consequently found that the neuraminidase derived from the bacteria of the genus Arthrobacter has a novel isozyme and that, when said neuraminidase isozyme S is allowed to act on gangliosides, ganglioside $G_{M1}$ can be selectively obtained with high purity and in good yield. According to the present invention, by-products are not produced, and therefore ganglioside $G_{M1}$ obtained can be readily purified. Further, the present invention has the advantage that ganglioside $G_{M1}$ can be prepared using said enzyme in the absence of any detergent.

The neuraminidase isozyme S (hereinafter referred to as "Isozyme S") to be used in the present invention has the following physicochemical properties :

(1) Action: Selectively producing ganglioside $G_{M1}$ from gangliosides.

(2) Molecular weight: About 52000 dalton

The molecular weight was determined according to gel filtration chromatography and SDS-PAGE electrophoresis as described below.

Gel Filtration Chromatography

Gel filtration method was conducted using Sephadex G150 (product of Pharmacia). As the eluent, 50 mM phosphate buffer was used.

SDS-PAGE Electrophoresis

Electrophoresis was conducted using SDS-polyacrylamide gel according to the method of U. K. Laemmli (Nature, 227, 680 (1970)).

(3) Optimum pH: 3.8-4.4 (when bovine brain gangliosides are used as the substrate)

(4) Stable pH range : 3.5-10.0

(5) Optimum temperature: 45°-55° C.

(6) Thermal stability: not higher than 60° C.

On the other hand, the neuraminidase derived from Arthrobacter ureafaciens was divided into type I and type II. Their physicochemical properties are as described in TABLE I below (Y. Uchida et al., J. Biochem., 86, 425, (1979)).

TABLE I

|  | I | II |
|---|---|---|
| Molecular Weight (gel filtration method) | 51000 | 39000 |
| Optimum pH | 5.0-5.5 | 5.0-5.5 |
| Stable pH range | 6.0-9.0 | 6.0-9.0 |
| Optimum Temperature | 53° C. | 53° C. |
| Thermal Stability | <50° C. | <50° C. |

The above description shows that Isozyme S is different from the conventional neuraminidase in physicochemical properties such as molecular weight, optimum pH, stable pH range, optimum temperature and thermal stability, and therefore they are enzymes of different molecular species.

The activity of Isozyme S is determined in the same manner as in the neuraminidase, for example, according to thiobarbituric acid method as described in J. Biol. Chem., 234, 1971 (1959)), etc. One unit of Isozyme S is defined as the amount of enzyme liberating 1 μmole of N-acetylneuraminic acid per minute at 37° C.

Isozyme S can be collected from the culture obtained by culturing a bacterium of the genus Arthrobacter.

As the bacteria of the genus Arthrobacter, known bacteria can be used. Examples thereof are strains of Arthrobacter ureafaciens such as Arthrobacter ureafaciens M1057 (FERM BP-1391).

The incubation of the bacteria of the genus Arthrobacter can be conducted using either conventional liquid or solid media, but it is generally advantageous to use a liquid medium. Incubation with shaking or incubation with aeration and stirring is preferably conducted in order to produce the desired enzyme. The media for the above incubation are not specifically limited, and there can be used various media containing nutrients and the like commonly used for incubating microorganisms. Examples of the nutrients are sugars such as glucose, fructose, lactose, invert sugar, saccharified starch solution, colominic acid, sorbitol and glycerol; organic acids such as pyruvic acid, malic acid and succinic acid, nitrogen sources such as peptides, meat extract, yeast extract, casamino acid, urea, ammonium salts and nitrate salts; inorganic salts of phosphorus, magnesium, potassium, sodium, etc.; trace elements such as boron, copper, iodine, iron, manganese, zinc, cobalt, molybdenum; trace growth factors such as vitamins; and so on. Further usable as the above media are, for example, natural or semi-synthetic media containing extract or exudate of animal tissues. Examples of these media are those marketed under the name of "Todd Hewitt Broth medium", "Brain Heart Infusion medium", etc.

Incubation was conducted generally at a temperature of about 20° to about 40° C., preferably about 25° to about 30° C. and completed in about 10 to about 70 hours.

Isozyme S can be prepared from the culture solution of the bacteria of the genus Arthrobacter in a conventional manner. For example, the bacteria are separated and removed from the culture solution, and the obtain supernatant is subjected to purification procedure such as ammonium sulfate fractionation and affinity chromatography and, if desired, may be further subjected to purification steps such as ion-exchange chromatography, chromatofocusing and gel filtration.

By allowing the Isozyme S thus obtained to act on gangliosides, ganglioside $G_{MI}$ is obtained selectively. Said enzyme reaction is conducted by adding Isozyme S to the starting solution containing gangliosides and buffer, and if desired, sterilized water.

In the above enzyme reaction, the gangliosides, i.e., the starting materials of ganglioside $G_{MI}$ are not specifically limited and there can be used known gangliosides. Examples thereof are at least one member selected from gangliosides $G_{DIa}$, $G_{DIb}$, $G_{TIa}$, $G_{TIb}$ and $G_{QIb}$, or a mixture of gangliosides extracted from bovine brain, etc. The amount of gangliosides is not specifically limited, and generally it is not more than 50 mg, preferably about 0.1 to about 3 mg, per ml of the starting solution. As the buffer, conventional ones having a pH of about 3 to about 6 can be used and examples thereof are about 10 to about 200 mM acetate buffer (pH 3.5–5.0), McIlvaine buffer (pH 3.5–5.5), etc. The amount of Isozyme S is also not particularly limited but can be widely varied. It is generally not less than 10 mU, preferably about 0.1 to about 10 U, per ml of the starting solution. The reaction temperature and pH are not limited so far as the enzyme is active, and generally the temperture can be about 20° to about 50° C. and pH can be about 3 to about 6. The reaction time is appropriately selected depending on the concentration of substrate, reaction temperature, etc. For example, the reaction time is 30 minutes to 24 hours at 37° C.

For purifying ganglioside $G_{MI}$ from the reaction solution, known purification methods can be employed. For example, purification can be conducted by subjecting the reaction solution to solvent extraction and then carrying out concentration, desalting, freeze-drying, etc.

EXAMPLES

The present invention will be described in greater detail with reference to the following reference example and examples.

REFERENCE EXAMPLE 1

In 2l-Sakaguchi flask was placed a medium (adjusted to pH 7.0) containing 5.0 g of lactose, 2.0 g of diammonium hydrogen phosphate, 3.0 g of sodium chloride, 1.0 g of dipotassium hydrogen phosphate, 0.1 g of magnesium sulfate and 1000 ml of deionized water. Then the medium was sterilized by heating in an autoclave.

This medium was inoculated with *Arthrobacter ureafaciens* M1057, followed by shaking culture at 28° C. for 24 hours. The culture solution obtained was centrifuged (10000 rpm, 10 minutes), giving a culture supernatant.

Subsequently, ammonium sulfate was added to the culture supernatant and the fraction precipitated when the ammonium sulfate was added to the supernatant to 80% saturation was collected. The precipitate was dissolved in a small amount of water, followed by dialysis against 10 mM acetate buffer (pH 4.5). The dialysate was passed through the column packed with the gel which was prepared by adding epichlorohydrin to 2N sodium hydroxide solution containing soluble starch and colominic acid and in which the colominic acid served as a ligand. The neuraminidase adsorbed was then eluted with 100 mM acetate buffer (pH 4.5).

The neuraminidase active fractions were subjected to salting-out with ammonium sulfate and dialysis against desalted water. The dialysate was separated into three components by chromatofocusing. The chromatofocusing was conducted as follows. The dialysate was passed through a column of polybuffer exchanger equilibrated with 25 mM imidazole-HCl (pH 7.4) using polybuffer 74 (product of Pharmacia) adjusted to pH 3.8 as eluent.

The three components obtained were independently subjected to salting-out with ammonium sulfate and dissolved in 100 mM phosphate buffer (pH 7.0). The solution was subjected to gel-filtration with Ultrogel AcA44 (product of I. B. F. Biotechnics), giving 4 components. Isozyme S (650 units) was obtained from one of these 4 components.

The enzyme activity of Isozyme S was determined according to thiobarbituric acid method as follows.

That is to say, 0.1 ml of the enzyme solution, 0.05 ml of 0.4% N-acetylneuraminyllactose solution and 0.05 ml of 0.2M acetate buffer (pH 5.0) were subjected to reaction at 37° C for 10 minutes. The amount of N-acetylneuraminic acid released was determined by thiobarbituric acid method. One unit of Isozyme S was defined as the amount of enzyme producing 1 μmole of N-acetylneuraminic acid per minute at 37° C.

EXAMPLE 1

A 1 ml quantity of 0.4% ganglioside $G_{TIb}$ solution, 1 ml of 40 mM acetate buffer (pH 4.0) and 1 ml of distilled water were mixed together, and to the mixture was added 1 ml of aqueous solution of Isozyme S (5 U/ml). The mixture was allowed to react at 37° C. for 1 hour, and 1/10 part by volume of chloroform was added thereto to stop the enzyme reaction. Ganglioside $G_{MI}$ was extracted from the reaction solution with use of a mixture of chloroform and methanol (2:1) and then lyophilized, giving 2.4 mg of ganglioside $G_{MI}$ as a white powder.

A thin layer chromatographic analysis under the following conditions indicates that the white powder obtained above shows a single spot of the same Rf value (0.48) as the authentic sample of ganglioside $G_{MI}$ (purity not less than 99%, product of Honen). Therefore, it was confirmed that the product was ganglioside $G_{MI}$ having a purity which is equal to or greater than that of the authentic sample.

Conditions of Thin Layer Chromatography

Thin layer plate: high performance TLC (HPTLC) No.5641 (product of Merck)
Developing solvent: mixture of chloroform, methanol and 0.02% $CaCl_2$ (60:35:8)
Color reagent: resorcin hydrochloric acid reagent

EXAMPLE 2

A 1 ml quantity of 0.2% ganglioside $G_{Dlb}$ solution, 1 ml of 40 mM acetate buffer (pH 4.0) and 1 ml of sterilized water were mixed together, and to the mixture was added 1 ml of aqueous solution of Isozyme S (3 U/ml), followed by reaction at 37° C. for 5 hours. Chloroform(1/10 part) was added to the reaction solution to stop the enzyme reaction. Ganglioside $G_{MI}$ was extracted from the reaction solution with a mixture of chloroform and methanol(2 : 1) and then lyophilized, giving about 1.5 mg of ganglioside $G_{MI}$ as a white powder. The production of ganglioside $G_{MI}$ was confirmed in the same manner as in Example 1.

EXAMPLE 3

The reaction and purification were conducted in the same manner as in Example 2 except that 1 ml of a solution of ganglioside mixture (containing 10 mg of the gangliosides) obtained by extraction from bovine brain was used as the gangliosides, giving about 6.2 mg of ganglioside $G_{MI}$ as a white powder. The production of ganglioside $G_{MI}$ was confirmed in the same manner as in Example 1.

We claim

1. A process for preparing ganglioside $G_{MI}$ selectively which comprises subjecting a solution of ganglioside or a mixture of gangliosides to the action of neuraminidase isozyme S obtained from a culture of a bacterium of *Arthrobacter ureafaciens* M1057, wherein the ganglioside or the mixture of gangliosides is at least one member selected from gangliosides $G_{Dla}$, $G_{Dlb}$, $G_{Tla}$, $G_{Tlb}$ and $G_{Qlb}$ or a mixture of gangliosides extracted from bovine brain.

2. A process according to claim 1 wherein the neuraminidase isozyme S is reacted with the ganglioside or the mixture of gangliosides by adding neuraminidase isozyme S to a starting solution containing the ganglioside or the mixture of gangliosides and a buffer.

3. A process according to claim 1 wherein the neuraminidase isozyme S has the following physicochemical properties:

Action: Selectively producing ganglioside $G_{MI}$ from gangliosides
Molecular weight: about 52000 dalton (according to gel-filtration chromatography and SDS-PAGE electrophoresis)
Optimum pH: 3.8–4.4 (when bovine brain gangliosides are used as the substrate)
Thermal stability: 60° C. or lower.

4. A process according to claim 2 wherein the starting solution further contains sterilized water.

5. A process according to claim 2 wherein the amount of the ganglioside or mixture of gangliosides is not more than 50 mg per ml of the starting solution.

6. A process according to claim 5 wherein the amount of the ganglioside or mixture of gangliosides is about 0.1 to about 3 mg per ml of the starting solution.

7. A process according to claim 1 wherein the amount of neuraminidase isozyme S is not less than 10 mU per ml of the starting solution.

8. A process according to claim 7 wherein the amount of neuraminidase isozyme S is about 0.1 to about 10 U per ml of the starting solution.

9. A process according to claim 1 wherein the reaction is conducted at a temperature of about 20° to about 50° C.

10. A process according to claim 1 wherein the reaction is conducted at a pH of about 3 to about 6.

* * * * *